US006656137B1

(12) United States Patent
Tyldsley et al.

(10) Patent No.: US 6,656,137 B1
(45) Date of Patent: Dec. 2, 2003

(54) VESTIBULAR AND RAS ENHANCING DEVICE

(75) Inventors: James Eugene Tyldsley, Royal Palm Beach, FL (US); Loran L. Swensen, South Jordan, UT (US)

(73) Assignee: Omega Assembly Trust

( * ) Notice: Subject to any disclaimer, the term of this patent is extended or adjusted under 35 U.S.C. 154(b) by 0 days.

(21) Appl. No.: 09/083,621

(22) Filed: May 24, 1998

Related U.S. Application Data

(63) Continuation-in-part of application No. 08/564,817, filed on Nov. 29, 1995, now abandoned.

(51) Int. Cl.⁷ .................. A61H 23/02; A61M 21/00; A63G 1/10; G09B 19/00
(52) U.S. Cl. ............... 601/15; 601/18; 601/49; 601/50; 601/86; 600/28; 472/29; 472/60; 434/185; 434/236
(58) Field of Search .................. 601/15, 18, 49, 601/50, 84–87, 112; 600/15, 21, 26–28; 472/29, 59, 60; 434/185, 236

(56) References Cited

U.S. PATENT DOCUMENTS

| | | | |
|---|---|---|---|
| 4,320,768 A | * | 3/1982 | Ledley et al. |
| 4,710,129 A | * | 12/1987 | Newman et al. |
| 4,728,293 A | * | 3/1988 | Kole, Jr. |
| 4,940,453 A | * | 7/1990 | Cadwell |
| 5,024,650 A | * | 6/1991 | Hagiwara et al. |
| 5,503,560 A | * | 4/1996 | Stentiford |

FOREIGN PATENT DOCUMENTS

GB    2258149    * 2/1993

* cited by examiner

*Primary Examiner*—Danton D. DeMille
(74) *Attorney, Agent, or Firm*—George A. Teacherson (57) ABSTRACT

Structure providing sessions of a prolonged spinning therapeutic modality that affects the biological occupant therein stimulating, exercising and strengthening the occupant's R.A.S in combination with other stimuli that affect the organism with different types of physiological and neurological stimuli such that several unique types of input affect the organism synergistically to provide a far greater therapeutic benefit than the prior art showed by using such stimulus devices individually.

50 Claims, 3 Drawing Sheets

VESTIBULAR AND RAS ENHANCING DEVICE

This is a continuation-in-part of the application Ser. No. 08/564,817 filed Nov. 29, 1995 now abandoned.

BACKGROUND OF THE INVENTION

1. Field of the Invention

The instant invention relates to mechanical organism stimulators and more particularly to a rotating device for providing synergistic benefits to an organism in "alternative" therapy; said therapy instantly stimulating Reticular Activating System, RAS, as its primary operation.

2. Description of the Prior Art

Devices for sensory enhancement and stimulation are multitudinous.

Organism body manipulators are shown in U.S. Patents to:

Vulliet-Durand, U.S. Pat. No. 3,258,008 for a "Rotary Seat for Medical Purposes." This is a chair that spins long enough to perform a "nystagmus test" and stops spinning after said test data are collected By the Graham Factual Inquiries, MPEP 2141, 2143, it gives no suggestion of RAS stimulation, nor spinning a body so to specifically stimulate the RAS, nor spinning a body in the correct position so to induce the synergistic effects herein disclosed. Nor is there any such contemplated use in the prior art. Neither is there any contemplation nor suggestion of any medical purposes other than recording brain waves. Any other holdings would be statements of impermissible hindsight.

Newman, et al., U.S. Pat. No. 4,710,129 for a "Simulation Device." This game can rotate in response to control stick movements. The same prior art neither contemplates such a use for rotation as herein provided, nor does it suggest that rotation itself would provide "user stimulation" as described herein the instant specification. Neither does it use the same or other instant "user stimulation" accouterments. It provides an enclosed environment for "simulation" of a game environment, not "stimulation" of a user's R.A.S. If the game simulates a plane continuously spinning, the game would end and stop with a simulated crash. No therapeutic modality would result. Any other holdings would be statements of impermissible hindsight, MPEP 2141, 2143.

Gorges, U.S. Pat. No. 4,315,502 for a "Learning-Relaxation Device." This is a simple goggle-driven device which teaches the ability to stimulate and "drive" brain waves. It is basically outfitted with pulsing lights and sound waves in both left and right sides of a user.

Levy, U.S. Pat. No. 4,640,266 for a "Sensory Stimulation Enclosure". This device is a completely enclosed chamber for "integration of an occupant's senses." Its purpose is for the relief of stress. It does not itself move.

Khabdrova, U.S. Pat. No. 4,893,615 for an "Oxygenation and Relaxation Cabin". It also does not move. It is a simple closed enclosure that cuts out the natural environment and provides its own along with "audio-visual relaxation means".

Hagimara, et. al., U.S. Pat. No. 5,024,650 for a "Stress Dissolving Refreshment System." It is static and provides means to change the state of consciousness of the user.

Shade, U.S. Pat. No. 4,258,706 for a "Muscle-Relaxing Reclining Chair". The device has movable parts which operate to relax an occupant's muscles. It then provides vibration and heat to enhance the process.

Kole, Jr., U.S. Pat. No. 4,728,293 for a "Learning Device." This is a movable device which is used to stress body cells beyond 1-G of force and thereby enhance learning. It is a reciprocating device and the G-Force stress is generated via its pulsing movement.

Contrarily to all of the above, the instant invention uses rotary, continuous spinning motion along with enhancing accouterments to provide therapeutic, synergistic stimulation to a user. Any inner electronic workings of any of such accouterments, that have not been patented already, are maintained as trade secrets. The instant application relates to a spinning chair, proper support of a body to be spun therein and the chair's accouterment devices. It is these structures and their combinations, which will be fully disclosed herein.

SUMMARY OF THE INVENTION

The instant invention is a soma-/neuro-therapeutic device for providing enhancement of body and mental conditioning to a user. Mechanical spinning is combined with synchronized accouterment devices to produce a result that provides behavior modification, stress management, accelerated learning, motor skill enhancement, and speech development plus biofeedback processing and the ability to bridge the objective and subjective mind. In the instant invention, therapeutic results can be obtained through the synergistic cooperation of at least one of several of the various accouterment devices acting along with the continuous, prolonged gross spinning motion of chair 10.

Accordingly, it is an object of the instant invention to provide a spinable body support device.

It is a further object of the instant invention to provide accouterments to the device that also stimulate an organism.

It is a still further object of the instant invention to provide optional, synchronizable accouterments.

It is another object of the instant invention to provide additional sensory stimulation to provide a synergistic result via a combination of accouterments that stimulate body and mind.

It is still another object of the instant invention to provide memory enhancement to a user.

It is still another object of the instant invention to provide accelerated learning.

It is additionally a further object of the instant invention to provide experiences of exteriorization.

It is still additionally a further object of the instant invention to provide ways to bridge the objective and subjective mind.

It is still additionally another object of the instant invention to provide a controlled system of continuously rotating a user in a prolonged orbit.

It is still additionally another further object of the instant invention to provide an organism a platform having a correct, comfortable supine position for enhancing therapeutic effect.

BRIEF DESCRIPTION OF THE DRAWING

Further objects and advantages of the instant invention can be found in the detailed description of the preferred embodiment when taken in conjunction with the accompanying drawings in which like numerals denote like elements, and.

DESCRIPTION OF THE PREFERRED EMBODIMENT

The Sensory Stimulus Chair 10 is seen in the several Figs. of the drawing. It has body support 11, itself supported on tripod (or other suitable) chair support 12. Within the confines of support 12 is electric motor 14, which is used to orbit or physically spin, rotate or twirl body support 11 via mechanical shaft 15. Body support 11 is angled to incline the body of the organism in a more therapeutic generally supine position. The apparatus has this preferred angle on body support 11 so as to effectively promote stimulating the RAS and is more effective than if the organism was seated in an upright position. The spinning motion of the device 10, by virtue of being continuously spinning throughout the therapeutic session, stimulates the vestibular canals in the inner ear of the user, further affecting the RAS and also increasing the blood flow and oxygen levels in the brain. It also produces a "timeless/weightless" feeling in the occupant. It furthermore enhances motor skills, coordination and speech development. The spinning motion is reversible in direction for use in the Southern Hemisphere. Additionally, it may also be made variable in speed. The user rests upon seatback 6. User enclosure or "hood" 17 is attached to body support 11 and is thus also simultaneously spun along with body support 11 by motor 14. It is preferably swingably attached, or hinged, at one end of support 11 so to provide vertical opening and closing actions to accommodate entrance and exit of the user to and from the device 10. All electricity needed to run the accouterment devices, and specifically those riding on spinning body support 11, and all computer data that is transmitted by wire is fed to chair 10 through rotating connector 125 which itself also spins. Rotating connector 125 handles all electrical connections made to the chair 10 and its accouterments. Rotating connector 125 is preferably at least a Model 630 or larger made by Mercotac, Inc. Computer 20 also has a preferably "flashcard"-type scroller for accelerated learning, which feeds its information into TV 30 via antenna 24 to antenna 25 via radio waves.

Figure 1:
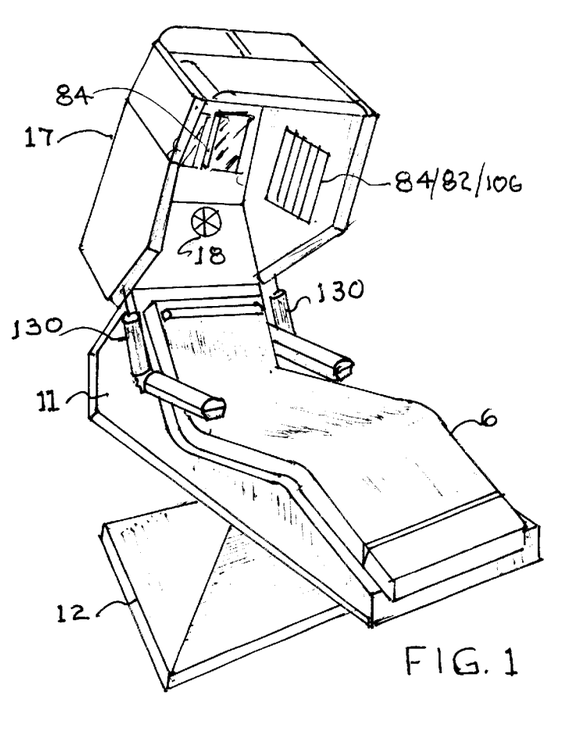
FIG. 1 is an oblique view of the stimulus chair of the instant invention.
Figure 3:
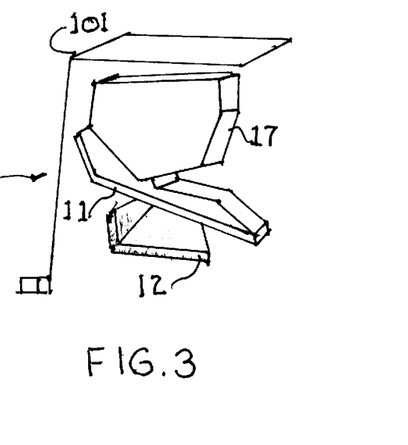
FIG. 3 is a side view of the chair of FIG. 1 with the hood closed and showing an accouterment device.
Figure 4:
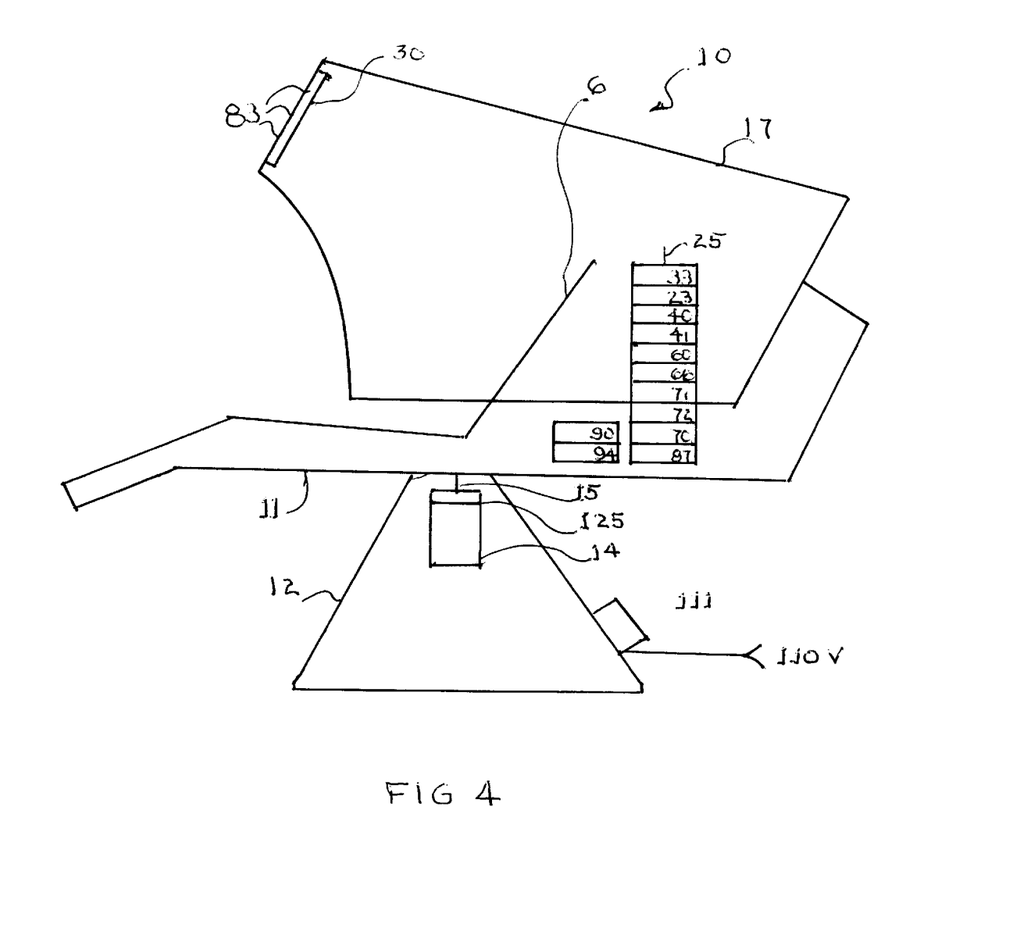
FIG. 4 is a side view of the chair of FIG. 1 shown cutaway to show normally hidden accouterments.

Hood 17 is provided with, at least, a fan 18 to deliver continuous fresh air to device 10's user.

Shock absorbers 130 are placed into position to facilitate the opening and closing and the distribution of weight of hood 17.

Figure 5:
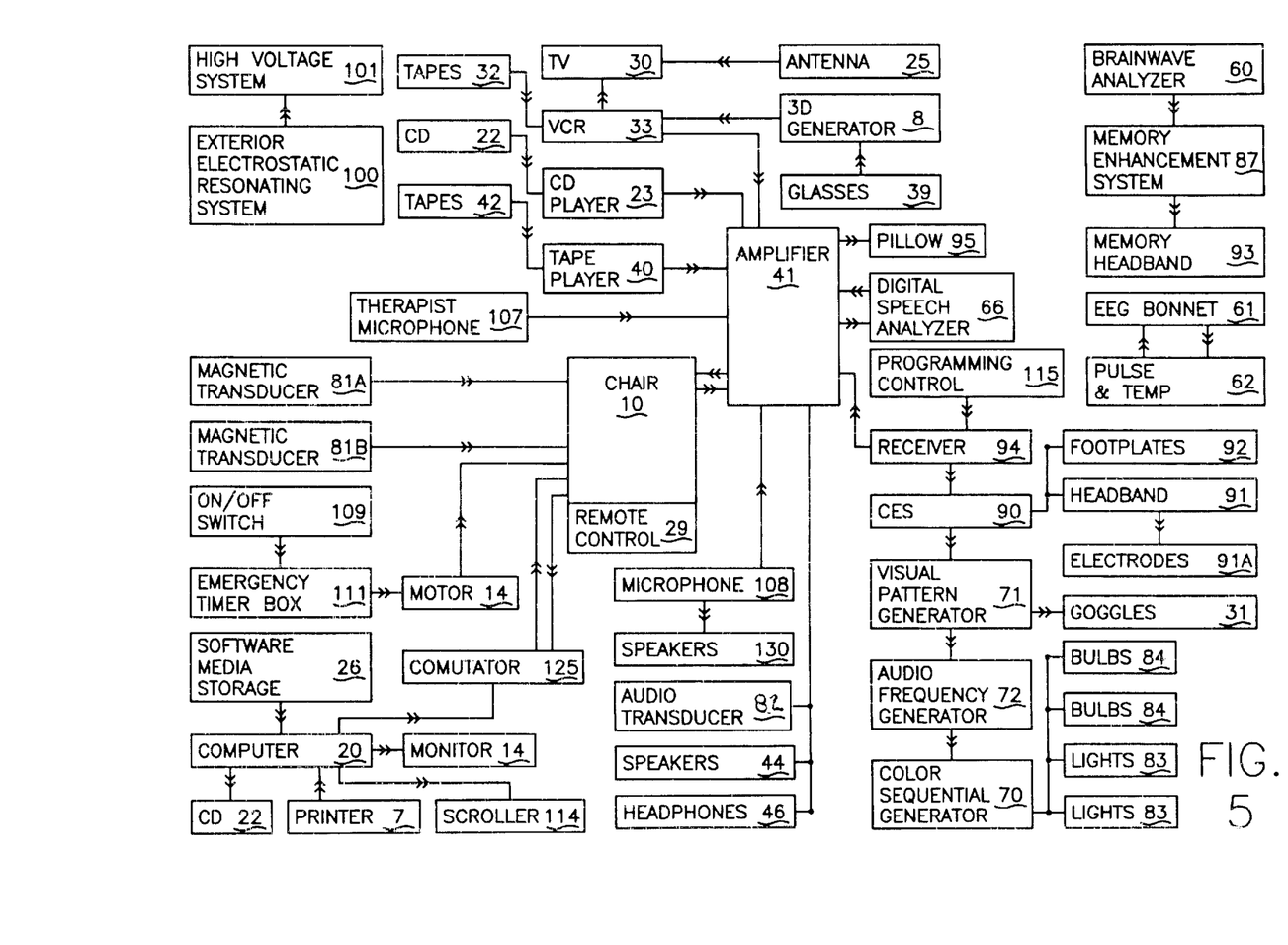
FIG. 5 is a schematic representation of the computer and the Chair's associated accouterment systems.

A two-way on/off switch 109 can be provided either to completely stop chair 10 from spinning by the attendant or for the user to summon an attendant for help via remote control device 29 while the user is inside chair 10 with hood 17 down.

Studies have shown that the Reticular Activating System (RAS) in the brain of an organism may be thought of as a "nervous energy reservoir" providing a significant part of the background facilitory energy upon which the body may accomplish its specific activity nerve impulses. Many studies have found the RAS to energize and modulate the responsiveness of the cerebral cortex. A generally supine position with passive, full-body, complex motion, such as, swinging in a hammock or even rocking in a chair, or active participative motion of the body, provides a gross motion treatment to the organism. Slow, rhythmic, repetitious movements have been shown to relax or provide a sleep-inducing effect. A state of health of a RAS not in condition may be properly enhanced via the stimuli of both G-force and motion and can be exercised, conditioned and strengthened by the increased amounts of energy that moving platforms supply. High-frequency, audible, monotonous sounds can vibrate the "labrynthes" of the vestibular (audio) canal and exercise the muscles of the middle ear. Low-frequency vibration of the spine is used to enhance the flow of nervous energy and relaxation. However, the studies show that complex, repetitive motion is the basis of treatment with all else being supplementary.

The R.A.S. is a true "neural net" with a constant and diffuse "nervous energy reservoir" which changes the cerebral cortical responsiveness of the brain. A prior art R.A.S. treatment protocol would be one of eyes closed, minimizing or absolutely no mental, emotional or physical movement coupled with generally supine, passive, full-body complex motion in a hammock or swing. Hence, in the instant invention, a correctly positioned generally supine user experiences continuous spinning, which provides the gross full-body complex motion. Gross, overall body motion has a valid neuroanatomical and neuropsychological treatment basis in the literature known to those skilled in the therapeutic art. Optimal session length for therapeutic RAS treatment has been shown in studies to be no less than 50 minutes of continuous repetitive motion. The benefit to the organism experiencing optimal sessions is cumulative and progressive. Add to that the instant synergistic application of at least one of several accouterment devices and the effect on the organism facilitates far-enhanced R.A.S. activity, neural pathway activity and enhanced cellular activity than the prior art could ever have conceived The instant claims all require a specific R.A.S.-stimulating device in cooperation with sensory presentations of learning, behavior, speech, and motor skills, etc. so to assure operability as claimed. The provision of spinning dedicated to R.A.S. excitation reeducates the emotional mind and limbic system. Activities of the subjective mind are stimulated and acquired through proper suggestion and proper strengthening of the biological body/mind connection.

Thus, it is seen that the instant invention provides a complex motion to an organism by a controlled, prolonged, correctly positioned, spinning of it. No prior art produces such a RAS stimulating result. Response to the instant RAS stimulating result alternative treatment exhibits new and/or strengthened synapses and also sensitization of the brain stem becomes stable; nervous-energy of the brain becomes normalized and overall the body exhibits remission of symptoms from a weak or impaired central nervous system.

Continuous spinning in a repetitive orbit exercises and strengthens the limbic system of the brain as well as activating and strengthening the RAS. The structural element disclosed and shown in the drawings which provides these functions is the spinning structure, motor 14, rotating connector 125 and chair 10 itself with its accouterments (see directly below).

Associated therewith the above are various accouterment devices for use in synchronization with the above and also with each other. They can be combined in various combined totalities, and used singly or together to synergistically produce a body and mind stimulating result, and/or therapeutic effect. This result is neuro-therapeutic in nature. It provides soma-therapy. It reduces, or allows a user to manage, stress. Learning is accelerated Biofeedback techniques may be enhanced. The devices may be used for behavior modification. Some of the synergy has been privately demonstrated to include detoxification and substance abuse modification. Preferably handheld programming control 115 and its associated receiver 73, which is preferably built into visual pattern generator 71 and audio frequency generator 72 and is located within the confines of hood 17, is provided to assure that all devices and the chair start simultaneously and in a synchronized manner. The programming control 115 may be operated by an attendant to the device 10, or may even be operated by the chair's own user. The exterior receiver head 94 is located upon body support 11 integrated with visual pattern generator 71 and audio frequency generator 72. Exterior receiver head 94 is provided for assured sensing of control 115. A preferably remotely controlled handheld on/off switch 109 is provided along with emergency timer box 111. Box 111 has a controller inside it which can reverse the chair's 10 spin direction and/or rotate it at variable rates of speed It also has a timer switch, which can end sessions at a preset time and/or stop the device 10 entirely (as in the case of emergency). The timer switch provides the ability to establish operations for optimal time durations for repetitive vestibular system stimulation to fully effect the RAS response.

Some of the accouterment devices privately shown useful for session-demonstrated synergistic enhancement are as follows:

Computer 20 with monitor 69 preferably has a radio link to TV 30 in chair enclosure 17 via antenna 24 and antenna 25. Other forms of chair 10 can have onboard computers 20 controlled by handheld programming control 115. Necessary software programs are used to operate computer 20 hardware and thus properly and efficaciously run the accouterment devices to produce a specifically desired result for any single, individual user—and said result is thus also changeable from user to user—and even session to session. Compact disks 22, CD-ROM and/or other software storage media 26, may be used to store and recall the necessary software for use of computer 20.

Television (TV) 30 is physically mounted on the front of the chair hood 17 in position to be viewable by a user while and during spinning.

Alternatively, TV 30 may be utilized by wearable electronically controlled three-dimensional glasses 39 or excluded by using goggles 31 which have at least one light source for providing visually stimulating sensory means. 3-D generator 8 sends a preset hertz signal to glasses 39 which allows the viewer three-dimensional reality video perceptions while watching TV 30. The package would preferably comprise a Realeyes 3D™ device.

TV 30 and glasses 39 may be provided with three dimensional software programs from computer 20 via antenna 24 and antenna 25, or by specially developed three-dimensional reality video tapes 32.

Software programs themselves may be provided to the computer 20 via compact discs 22, or other, programming means such as a computer modem.

Videocassette recorder 33 may also be used in the combination to provide visual, three dimensional reality video, or two-dimensional video stimulation. This would operate normally via use of videotapes 32.

Audio tape player 40 and sound amplifier 41 may play tapes 42 to be outputted to speakers 44 and/or audio headset 46. Similarly, sound amplifier 41 may also output to speakers 44 and/or audio headset 46 information from all other devices VCR 33 and CD player 23.

Computer 20/monitor 69 can be used to monitor body responses to programmed stimuli via electro-encephalogram (EEG) brain wave analyzer 60 and/or digital speech analyzer 66 digitally monitoring speech frequencies. Same would be displayed on monitor 69 and recorded on computer software media 26. EEG information would be collected in the usual manner via 4-channel EEG bonnet 61. In addition, and to further collect information on body responses, pulse and temperature pickup 62 may typically be used on the subject's fingers, or, in the instant case, bonnet 61. Printer 7 can provide hard copy.

Bodily and/or mind sensory stimuli and the delivery of therapeutic information can then be provided to a using organism via the various accouterment devices such as the following:

Visual pattern generator 71 and audio frequency generator 72 provides light and sound stimulation. Same are preferably coupled to work together to provide synergistic results. Light, as may be delivered to the eyes via goggles 31, hits the retina of the eye, is converted by the retina to electrical energy which travels to the brain. This has a balancing effect on the two body chemicals, serotonin and melatonin. This helps balance emotions.

Light and sound stimulation is programmable with variable and adjustable intensities. The programs are of various types, supplying a range of frequencies and other programmable frequencies of light and sound, which allow various individuals varying experiences. These experiences result in accelerated learning, alpha, beta, delta and theta states of mind, suggestive states, euphoric states, "neuro-aerobics" to name a few.

Audio frequency generator 72 can also provide vibrational therapy beyond the range of human hearing. It works best in conjunction with visual pattern generator 71 to stimulate various types of experiences. Computer 20 determines what required frequency(ies) needs to be delivered to the user. Audio frequency generator 72 also works in concert with digital speech analyzer 66 to deliver required audio frequencies to the user. It then, via trade secret methods, can "fill in the blanks" by output to the body of those frequency (ies) generated by computer 20 and delivered via the audio transducers 82.

Color sequential generator 70 is used to provide color therapy. Color therapy is accomplished through a series of lights, controlled by a computerized program, which are situated on the left and right side of the user under hood 17. Same may alternatively be situated on the inside roof of the hood 17. Full spectrum fluorescent bulbs 84 preferably deliver the color. Bulbs 84, fitted with color filters, are controlled sequentially by computer software. Additionally, bulbs 84 are preferably enhanced with variable piggybacked hertz frequencies.

Preferred piggybacked hertz frequencies are programmed and selected sequentially to enhance standardized color therapy sessions and provide a condition of efficacious frequency absorption to any individual user.

Adjacent to and on either side of TV 30 are lights 83, which are not frequency programmed. Instead, they are activated in sequential patterns of color by computer to assist in inducing the registration in the user's brain of visual information being viewed on the screen of TV 30. These lights 83 act as a subliminal input driver 83 which allows the subject to deeply seat information in the levels of the subconscious mind.

Figure 2:
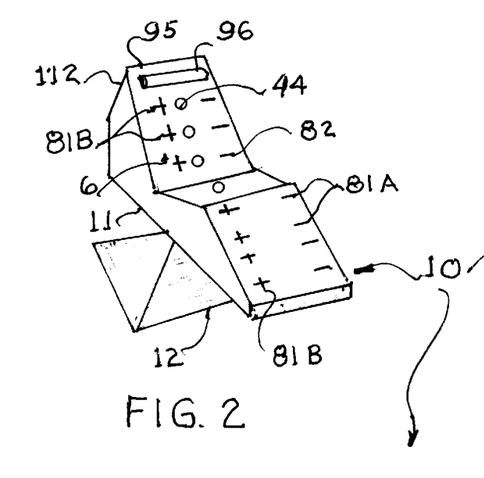
FIG. 2 is an oblique view of the chair of FIG. 1 with its hood taken off and showing the cushion.

The cushion 6 of chair 11 also has sound transducers 82 alternating with speakers 44. Magnets and/or magnetic transducers 81 would preferably be aligned down a user's spine with negative polarities 81A on the left side and positive polarities 81B on the right side. In addition to creating polarity conditioning for the body, the chair 10 may also arrange frequencies of sound for the body delivering that sound in deep, penetrating vortex patterns. Optionally, magnets 81 may be movably detachable so to accommodate different sizes and body types. Similarly, polarity magnets 81 can be movable and detachable so as to be arranged at predetermined focal points along the body. This allows for accommodating very young, very small individuals and also very large body types.

Memory enhancement system 87 has two electromagnetic transducers that are physically placed over the temporal region of the brain via memory enhancement headband 93 which feeds information to the user's brain. Computer 20 programming of different magnetic frequencies into transducers 87 causes the subject to enter into different states of mind, i.e.: a memory regression, not just a hypnotic state, and the individual goes back to relive past memories. These applied frequencies are not uniform and every person has their own frequencies which generate memories. This has basis from studies done at Laurentian University and others. Once the frequencies are found, they can be logged into computer 20 memory banks or software media 26 and played back to the individual during any session through the electrical-magnetic memory enhancement headband 93. This design is useful to induce memory regression for emotional reconditioning and trauma repair. Thus, the memory enhancement means 87 is strictly to induce memories via the application of frequency to the brain temporal region through headband 93. Chair 10 has capability for the attendant/therapist to speak to the chair's 10 user via microphone 107 to audio headset 46 to counsel as needed. The user, while on chair 10, also has lapel microphone 108 to allow the user to talk to the chair's 10 attendant/therapist. Microphone 108 feeds to a typical outside speaker 130. Just prior to getting on the chair 10, and for establishing a voice history, the user records his or her voice via voice microphone 107 to the digital speech analyzer 66 to store speech patterns in computer 20 and software media storage 26.

Sound transducer 82 is used to provide sound to the body of a user. It delivers sound energy in a vortex manner deep within the body. Speakers 44 merely enclose the body with sound ranging from 0–20,000 Hz.

A movable and detachable transducer pillow 95 is provided for utilization at the base of a user's skull regardless of their height. This accommodates all user height requirements. It allows sound and/or frequencies to be specifically applied at the brain stem for the purpose of effecting mind enhancement programs. This is removably attached to the chair 10 specifically by a standard prior art electronic cable 112 and is stretched between chair 10 and pillow 95. It is driven by a computer-enhanced signal which derives from the audio frequency generator 72 via amplifier 41.

An exterior electrostatic resonating system 100 can be provided as an option to device 10. System 100 is a computer board that provides an adjustable hertz frequency signal to high-voltage system 101. In the electrostatic resonating system 100, electrical high-voltage system 101 is provided above chair 10 at the base of the ceiling of the room enclosing the chair 10. Its energy is piggy-backed with an adjustable frequency. This system 100 is providing means to create a timeless/spaceless personal perception in the user of the chair 10. Additionally, the cranial electrical stimulator 90 promotes an endorphin burst affecting the pineal gland. Together, these two accouterments are further capable of enhancing the timeless/spaceless perception that is also generated by the spinning motion of the chair 10 itself. In the preferred embodiment, a consistently pulsating high voltage, low amperage direct current signal is maintained in system 101. A low-end, adjustable, earth-resonating hertz frequency from system 100, between 7–14 Hz, is piggy-backed onto the high voltage system 101 to induce an experience of exteriorization.

Studies involving Microwave Resonance Therapy have been shown to automatically take into account the above variables through applied frequency(ies) and to subjectively influence feelings and imagination. Extremely high frequency electromagnetic waves have been shown to have an impact on biologically active points far removed from the point of application. Studies have shown that living organisms with the human body in particular as the living system with the greatest number of variables and internal links, are all able to maintain their stationary state of equilibrium naturally. The human body can differentiate between applied frequencies with a high quality of merit in its reactions. Results of tests have shown significantly more speedy healing and increase of body protective forces.

Thus, when two energy systems (100 and an organism) are in tune or in resonance with each other, there is an energy transfer from one to another. Tuning fork resonance is an example of the process. The organism in the chair will resonate with the combined energy of the interior resonating energy in the chair and the exterior resonating system 100—FIG. 3—and consequently be biologically strengthened in self-sustaining effects.

Electrostatic resonating system 100 works in combination with the movable transducer pillow 95. During the time they are in use together, pillow 95 is being used at the base of a user's skull providing the range of frequencies from 7–14 Hz which would be selected per individual user. This then allows that user to undergo an immediate exteriorization experience. The resulting perceived distortion of time and space enhances the total body-mind experience.

Alternatively, another means to place the user in resonance is to bathe the body in frequency vibrations supplied by preferably five separate sound frequency programs and/or generators 72. The resonating sound system 102 of generators 72 with two transducers 82 each must generate sound via separate and different mathematical equations. Frequency programs and generators 72 may be computer driven by programmable selections of programs. Or, as an alternative, the frequency programs and generators 72 themselves may have predetermined software, such as have the light and sound programs. The various octaves derived from each generator 72 harmonize together to deliver the same frequency derived from the different octaves for a combined, desired, final, therapeutic effect that is delivered to the organism via the transducers 82 and their resonating drumskin covers 106. The transducers 82 of resonating sound system 102 lie to the left and right of the organism. These work in combination with the transducers 82 at the base of the skull, pillow 95, and in the body support 11. The drumskin covers 106 dimensionally enhance the resonating capacity of the entire chair system.

A separate amplifier must power the resonating sound system 102, which is the same type as amplifier 41.

The resonating sound system 102 can also be used in combination with the pillow transducers 95, body support 11 transducers 82 and electrostatic resonating system 100 such that one supports the other thus enhancing the tuning fork principle and making the combined systems use synergistically more effective.

The electrostatic resonating system 100 can have optional utilization of additional frequencies—which when used in combination with high voltage system 101, transducer pillow 95 and audio transducer 82 and even resonating sound system 102—generates specific signals ranging between 0 and 10,000 Hz. These signals can be utilized in the generated field, electrostatic and/or electrostatic plus audio, as a health-related benefit for an organism that is spinning in chair 10 normal to the field lines. This entirely optional combination of accouterments which combines electrostatic field and sound vibrations can enhance health. The combination entirely bathes the body in frequency vibrations— both resonating electrostatic and audible.

Additional stimulation is provided by cranial electrical stimulator 90, which has a programmable range of frequency. It is preferably applied via CES headband 91 through preferably silver electrodes 91A. This is specifically to stimulate a user's mastoid bones, and thus and thence the vestibular nerve. This electrical stimulation may alternatively be applied to a user's feet via footplates 92. The programmable range of frequencies is applicable to conditions of stress, anxiety, depression, pain management and other conditions. Stimulator 90 is preferably of a type that can automatically monitor and detect changes in a subject's skin through electrodes 91A, thus automatically changing its own output so that a user's session remains consistent.

"Tachyon energy" can ostensibly be harnessed according to the maker of "Optimum Resonant Material" materials made by Tachyon Energy Research, Inc. To paraphrase the firm's explanatory information: The materials have been specially processed to create or stimulate a metamorphic change at the quantum molecular level, giving these materials an antenna-like ability to focus tachyon energy of specific 4–16 micron wavelengths. These wavelengths are vital to maintain optimum cellular metabolism, helping to organize the body's water molecules, giving better oxygen flow and absorption of important nutrients and minerals into the body's cells. These materials can be coated onto special ultra-thin fibers that can be woven into a fabric covering.

Relying on the above information, the "tachyon" fiber cover 96 would preferably cover everything a user is lying upon and would insure the efficacious stimulation of the user by the product and be a thoroughly useful accouterment device.

The prior art has not understood the synergy of utilizing all the basic elements: cranial electrical stimulation, light and sound, "tachyon" stimulation, spinning, color therapy, frequency vibrational therapy and magnetics to provide synergistic stimulation as the instant chair 10 does. Same have not suggested its combination, neither have they given any evidence that same have even contemplated such a device.

Speech, motor skills enhancement and behavior modification occurs as the spinning and other stimuli work together in creating biological changes in the descending and ascending R.A.S. that people do not normally undergo. Normally, while in an upright state or standing, an organism utilizes the greater per cent of brain activity balancing against gravity utilizing muscle strength and coordination. While in a properly positioned session of spinning, no attention is necessary to these details, and all attention is focused on the absorption of stimuli and information.

The ascending R.A.S. stimulates the limbic system and emotional mind, thus enhancing behavior modification through the upper cerebral cortex. The descending RAS stimulates speech, enhanced spinal reflexes, modulates responsiveness of the muscles and coordination. It also relaxes facial features, which becomes important in certain states of health (e.g.: mongolodism). The chair 10's environment creates and more effectively flexes and progressively strengthens the biological stability and learning capabilities of the user. These changes are related to increased RAS activity. This increased RAS influence is directly resulting from the chair's synergistic therapeutic output. And although the prior publications show such findings, nothing in the prior art addresses the synergistic boost in this enhancement function that the chair embodiment delivers to an organism.

It is known that all the bodily functions are under the control of the central nervous system. Man can not only govern the course of his mind but also can govern the actions of his body. This capability is probably alone among the animal kingdom.

The reflex nerve centers carry on the processes of the organs and body parts and represent centers in which a part of man's total mental organism is located Impulses sent from these centers are intelligences from an intelligence instead of mere mechanical operations. This is proved by recent findings on neuropeptide activity (per Dr. Candace Pert). The subjective mind has absolute control of the functions, conditions, and sensations of the body and also the subjective mind is amenable to control of suggestions. The potential of the subjective mind to make use of the reflex centers with their powers over functions and conditions provides the capabilities or channel through which man's will may reach to bodily conditions. One such channel is autosuggestion.

IN OPERATION, a user would simply lie down on body support 11 of device 10. The user would preferably then be outfitted with the requisite accouterments which could be used to give the synergistic results desired in any particular session.

How device 10 works is explained as follows: The activities of the subjective stratum of mind are stimulated and acquired through the proper suggestion via audio or video input in an environment which strengthens the biological body/mind connection utilizing various types of stimuli such as but not limited to: the R.A.S. from gross motion, the neural pathway activity via cranial electrical stimulation, and light and sound for enhanced mind entrainment, enhanced cellular activity throughout the body via Takionic® stimulus, magnetics and transducers.

As an example, in the instant invention, a subject who might have an emotional trauma pertaining to guilt, fear or anxiety and does not have knowledge of modifying such impulses could receive tremendous benefit and conditioning by utilizing the chair 10 and one of several of the accouterment devices. The overall rotating motion at minimum would stimulate the RAS. The light and sound stimulate neural pathways as well as "entrain the mind" to induce hypnosis. The cranial electrical stimulation selection of appropriate hertz signals known by those skilled in the art and applied to the mastoid bone would stimulate an endorphin release that would relax the subject and produce euphoric sensations as well as physiologically balancing and conditioning the sympathetic and parasympathetic nervous system. This results in a relaxed subject, who, while in a lucid, dreamy state of awareness, can effectively bridge between the objective and subjective minds. Objective audio input of select information would provide additional conditioning for emotional release and strengthening and balance of the emotional mind.

The input of specific instructions of subliminal or hypnotic nature would then be realized synergistically; far more quickly and easily. Conversely, if one were to listen to subliminal tapes without the use of the invention, one may have to listen many times, up to 25 times in succession just to begin to evidence the effect. The instant synergistic applications makes one readily responsive while in the chair 10 to the body/mind functions and their improved conditions outside the chair 10 will contribute to a stronger will and an increased confidence in self and in life.

One skilled in the art would use an assortment of provided programs within the light and sound, cranial electrical stimulation and audio input information and modulate the intensity of the experience provided by the accouterments and their proper adjustments. Audio/visual programs could be human potential tapes or educational format tapes.

Various new combinations and adjustments of intensity of accouterments with R.A.S.-exciting spinning are being claimed.

Ideally, firstly, CES flexible metal headband 91 would straddle the head and silvered electrodes 91A would press against the user's mastoid bones.

Secondly, goggles 31 would be placed in front of a user's eyes and held in place by a typically adjustable headband strap.

Thirdly, audio headset 46 would then be placed over the previous two accouterments.

At various times, other accouterment devices such as EEG bonnet 61 and/or memory enhancement headband 93 in use with goggles 31 may be substituted for the previously enumerated ones.

Three dimensional glasses 39 may replace goggles 31.

Device 10 can help an individual learn, comprehend and retain new information at a highly accelerated rate. Tapes 42, CD's 22, and videotapes 32 on any subject may be played during a session. The spinning device 10 coupled with the sound, light and color accouterments 70, 71, 72 and 83 make a user's mind especially receptive to the played information. By synchronizing the two hemispheres of the brain and lowering brain waves to the trance-like theta pattern, device 10, via generators 70, 71, and 72 induces a deep meditative state in the user, increases blood flow to the brain as well as oxygen, endorphins and other brain chemicals. Thus increased creative thinking and deep body sensations are induced with the individual becoming highly alert and aware.

Since the theta patterns are linked in contact directly into the subconscious mind, the played information is positively implanted at optimum brain receptivity and thus the information is retained at a very high percentage rate. The instant mechanical system with accouterments provides a bridge between the objective and subjective user's mind.

In the instant invention, therapeutic results can be obtained through the synergistic cooperation of at least one of several of the various accouterment devices acting along with the gross continuous spinning motion of chair 10.

The user of device 10, experiencing an alpha brain signal induced from the generators 70, 71, 72, and 83 can "subliminally photograph" information from a software database, via TV 30 and be retained at a very high percentage rate. The information from computer 20 can be displayed to the user on TV 30 at variable rates of speed from 1 second per page to 30 seconds per page. This is done via flash scroller 114. This system allows the user to scroll through the displayed information at a speed that is adjustable to an efficacious setting utilizing alpha-brainwave-entrainment patterns from computer 20 to retain the information at high speed. Thus, it is called "subliminal photography." Furthermore, the system allows the user to acquire skills of speed-reading. The prior-mentioned flashing color lights, subliminal input driver 83, can further enhance this subliminal photography session.

Although a regular computer scrolling system could present material, the prior art devices only present information by either the user or an operator manually timing the flash presentations and then manually scrolling via the keyboard, mouse or other computer-activating device. The best presentation of material for "subliminal photography" is when presented in a flashcard manner. And only flash scroller 114 [a trade secret device as a "black box"] provides that function automatically and most effectively.

Other patterns and signals are derivable from computer 20 memory banks and programming for additional states of altered consciousness.

All the accouterment devices working in concert with body support 11 and hood 17, synchronized together by the computer 20 into essentially one complete device 10, set up parameters and work in sync with each other to produce the individual desired synergistic result.

Such synergistic results can take the form of behavior modification, stress management, accelerated learning, motor control and speech development, plus biofeedback processing.

Thus it is seen that device 10 has combined and synchronized several effective devices into one highly sophisticated, powerful and novel soma-/neuro-therapeutic device 10 that produces truly advanced mental conditioning and body-mind therapy.

Such therapies can take the form of:

Vestibular Stimulation. This is the direct result of spinning the occupant of the device 10. Ohio State School of Medicine studies showed that vestibular stimulation of sorts do enhance motor skills, coordination and speech capabilities.

Cranial Electrical Stimulation. This accouterment 90 stimulates endorphin production electrically and helps the brain return to normal chemical balance without itself using chemicals. Information such as this was published in the magazine *Diseases of the Nervous System*, and many others. Instantly, it is preferably completely computer driven and software controlled This assures individualized and "perfect" synergy for each particular user.

Brain Wave Analyzing. Typically the device 10's analyzer 60 would preferably monitor some 5,500 different frequencies in both the left and the right hemispheres of the brain, muscle tension and heart rate. All this information can be displayed on the device 10's command console monitor 69, from software media storage 26 and may always be printed out during or after the particular session. The information travels via prior art computer cable through rotating connector 125 from brain wave analyzer 60 to computer 20, as well as from digital speech analyzer 66 to computer 20. The same line through rotating connector 125 is preferably utilized to computer 20 for collecting both types of data.

Specialized biofeedback games can be programmed with brainwave analyzer 60, TV 30 and computer 20 to provide teaching for brain wave self control of alpha, beta, theta and delta patterns.

Audio Frequency Generation. A gentle pulsing tone relaxes the body and guides brain wave activity towards a selected brain entrainment pattern and maintains that state throughout the session. It calms the brain and frees the mind while inducing a deep meditative state. Thus, the mind is extremely relaxed, yet extremely alert and receptive.

The amplifier 41 enhances the sound of the audio frequency generator 72 and the sounds from the VCR 33 or audio tape player 40 as well as CD 22, and delivers a sound to the user that has been proportionately balanced to the audio transducer 82 and speakers 44, pillow 95 and audio headset 46. In addition, amplifier 41 delivers sound from microphone 107 to the user.

Additional amplifier 41 is used to enhance delivery of resonating sound system 102.

Visual Pattern Generation. Flashing preferably full spectrum white lights synchronized with the audio frequency generator 72, the visual pattern generator 71 relaxes the body and soothes the eyes. Studies from Tokyo University, and others, show that such "flickering lights" cause the brain to produce endorphins for the stimulation of creative thinking and a series of deep body sensations. Thus, the lights affect two brain chemicals serotonin and melatonin and thence the moods and overall sense of well being of the organism experiencing the device 10.

This result is especially valuable in cases of individuals undergoing the severe physical and psychological stresses of detoxification or brain chemical imbalance.

Digital Speech Analyzer 66. Detects the presence of all frequencies, or lack thereof, present in the human voice. It records them in real time to the Computer 20. Any frequency not present in an individual's voice is then generated and those specific frequencies are played back through the sound transducers 82. Thus, transducers 82 provide body-enhancing frequencies.

Reality Video Presenter. Reality three-dimensional videos can be played to a user via videocassette recorder 33 and TV 30. Hence, martial arts, sports, dance, etc. body movements can be taught subliminally, producing more highly efficient skills in a reduced time period. The structural element of the "reality video presenter" is a three-dimensional viewing package. The package would preferably comprise a Realeyes 3D™ device. Said device converts the normal television or video 2-dimensional signal into a three dimensional stereoscopic display. This provides the invention 10 with versatile presentation capabilities.

Audio Programming, of subliminal or hypnosis tapes. Combined with visual and cranial stimulation, and behavior modification becomes even more powerful. Here is where device 10 can be outfitted with multimedia capabilities to produce accelerated final results.

Stress Management. Device 10 incorporates many accouterments that can help a user achieve mental and physical relaxation. This directly relieves the effects of stress to the body and mind.

Behavior Modification. Habit changes represent the effective treatment results of the user's continuing progressive and accumulation of benefits derived from mind entrainment of the spinning motion combined with light, sound, audio and/or visual programming over a period of time. Usually amounting to some 28 days, at minimum, continuous repetition has been shown to produce life-enhancing changes. As verified in studies from Harvard University and others, animals and people exhibit a learned behavior or what is known as "premature cognitive commitment." These conceptualized structural boundaries of the mind are established by reinforced cumulative life experiences, which affect the organisms' judgment systems. They limit the belief systems and the individual's recognition of stimulations or choices.

Stored energy of the mind that is of a degenerative nature violates the body's tissue integrity and thereby is established as the ultimate root of disease. With the release of negative, precognitive conditioning, replacing it with new choices or new structural awareness by therapeutic excitation of the RAS, the instant invention 10 opens the pathway for healthful change. Neuropeptide activity binds information to the receptors of every cell of the body. With the reeducation of the mental processes, the mind is capable of sending thousands of interpretations of mental thought through the aforementioned neuropeptide activity. This allows previously limited interpretations of stimuli to be automatically perceived and responded to by the organism. Thoughts and stimulation to the body, mind and spirit that had previously been self-denied by the rigid, structured, self-imposed limits of belief can now be accessed, reconditioned or reinforced.

In sum, device 10 (whether having fixed or repositionable seatback 6) accelerates the understanding of instruction in concepts of human potential and alters an individual's perceived, structured boundaries of the mind. Device 10 sensory stimulation modulates change in the development of an organism. It does this via applied fields of energy and the user's interpretation of ideas, or the biomechanics of thought. Thus, it transforms the boundaries of structural awareness; altering the individual's physical, spiritual and emotional realities. These results can be achieved through the synergistic cooperation of the various accouterments with the gross spinning motion of the chair 10. NO prior art known to inventor has placed specific frequencies of light and sound and cranial electrical stimulation or the other accouterment devices in an enclosed environment moving object. Nothing in the prior art shown acts for healthful change proactively as does the instant invention.

Perceptions in the user, such as timeless-spaceless experience, are synergistically created by use of one of several light and sound programs designed to facilitate an out-of-body experience. The spinning of the chair 10 facilitates the feeling of floatation as well as exciting the R.A.S. The cranial electrical stimulator 90 allows for programs that excite endorphin release. The movable transducer pillow 95 and the resonating sound system 102 may be used in combination with the exterior resonating system 100, electrical high voltage system 101 to provide a programmable frequency for resonance conducive for supporting many programs as well as exteriorization from the body. Thus a timeless/spaceless perception results.

Although various modifications may be seen, suggested and defined by those skilled in the art, it is to be understood that many modifications can be made thereto without departing from the spirit and scope of the invention as disclosed and defined herewith by the appended claims, thus,

We claim:

1. The process for activating, strengthening and enhancing the RAS, modification of upper cerebral cortex and strengthening the limbic system of a user, comprising:

Providing means for spinning said user;

Providing means for said spinning to occur in one direction only for the entire length of any one therapeutic session;

Providing said therapeutic session to occur over a length of time sufficient to enhance the RAS, modification of upper cerebral cortex and strengthening the limbic system of said user;

Providing means for supporting said user's body at an angle between vertical and horizontal for enhancing the RAS, modification of upper cerebral cortex and strengthening the limbic system of said user;

Providing an accouterment device onboard said chair for sensory stimulus to said user.

2. The process of claim 1 wherein there is provided simulation to enhance and strengthen said RAS, modification of upper cerebral cortex and strengthening the limbic system of said user where said process progressively eliminates through repeated spinning sessions brain disorders directly creating benefit to enhance a user's state of improved being.

3. The process of claim 1 wherein there is provided means for eliminating stress.

4. The process of claim 1 wherein there is provided means for stimulating one's ability to learn at a faster rate.

5. The process of claim 1 wherein there is provided means for balancing neuroanatomical and neuropsychological conditions of the brain.

6. The process of claim 1 wherein there is provided means for reintrainment and enhanced capacity of neural pathway activity.

7. The process of claim 1 wherein there is provided means for motor skill enhancement and speech development.

8. The process of claim 1 wherein there is provided delivery of frequency vibrations via means for audible and resonating electrostatic vibration generation.

9. The process of claim 1 wherein there is provided means for conditioning said user's brain for emotional release and strengthening and balancing the emotional mind.

10. A sensory stimulus chair for synergistic enhancing stimulation of an organism, comprising:
   a chair;
   said chair supporting said organism at an angle between vertical and horizontal to better synergistically stimulate the RAS of said organism;
   means for providing continuous, single-direction rotation of said chair over an extended length of time including timer means for providing optimal time duration sufficient to enhance the RAS;
   at least one separate accouterment device carried onboard said chair;
   said at least one separate accouterment device providing means for sensory stimulus to said organism;
   said sensory stimulus providing means for said synergistic stimulation of said organism;
   said means for providing continuous, single-direction rotation having a body support for said organism's body;
   chair support supporting said body support;
   mechanical shaft upon which said means for providing continuous, single-direction rotation spins;
   commutator mounted upon said mechanical shaft as means for directing multiple electrical signals to different ones of said at least one separate accouterment device carried onboard said chair;
   said mechanical shaft directly spinning said chair support; and
   means for spinning said mechanical shaft.

11. The stimulus chair of claim 10 wherein at least one magnetic device is carried onboard said chair and said at least one magnetic device is providing means for sensory stimulus to a user.

12. The stimulus chair of claim 10 wherein said at least one separate accouterment device has means for providing multiple therapeutic effects that stimulate biological processes in said organism in combination with differing hypnotic suggestion resulting from different ones of said at least one separate accouterment device delivering video and also audio information to said organism.

13. The stimulus chair of claim 10 wherein said chair provides means for an interface of synchronicity between functional sections of the brain, providing means for stimulating implanted mental information as directed commands between the objective and subjective minds.

14. The stimulus chair of claim 10 wherein said means for synergistically stimulating the RAS provides means for progressively conditioning and thereby enhancing said reticular activating system.

15. A sensory stimulus chair for synergistic enhancing stimulation of an organism, comprising:
   at least one separate accouterment device carried onboard said chair;
   said at least one separate accouterment device providing means for sensory stimulus to an organism;
   said sensory stimulus providing said synergistic enhancing stimulation of said organism;
   means for continuously spinning said organism in a repetitive, non-stop orbit until a session or efficacious preprogrammed use of said chair is over;
   said means for continuously spinning providing means for exciting reticular activating system of said organism;
   said means for continuously spinning having timer means for providing optimal time durations for repetitive vestibular system stimulation to fully effect reticular activating system response of said organism;
   said means for continuously spinning having a body support for said organism's body;
   said body support mounted at an angle between vertical and horizontal;
   said body support is means for exciting reticular activating system of said organism;
   chair support supporting said body support;
   mechanical shaft upon which said means for spinning spins;
   rotating connector as means for directing multiple electrical signals to different ones of said at least one separate accouterment device carried onboard said chair;
   said mechanical shaft directly spinning said chair support; and
   means for spinning said mechanical shaft.

16. The stimulus chair of claim 15 wherein at least one magnetic device is carried onboard said chair and said at least one magnetic device is providing means for sensory stimulus to said organism.

17. The stimulus chair of claim 15 wherein said means for spinning said organism has means for providing multiple therapeutic effects that stimulate biological processes in said organism in combination with differing hypnotic suggestions resulting from different ones of said at least one separate accouterment device delivering video and also audio information to said organism.

18. The stimulus chair of claim 15 wherein said chair provides means for an interface of synchronicity between functional sections of the brain, providing means for stimulating implanted mental information as directed commands between the objective and subjective minds.

19. The stimulus chair of claim 15 wherein said means for exciting reticular activating system provides environmental means for conditioning and strengthening said reticular activating system.

20. The chair of claim 15 wherein said means for exciting reticular activating system comprises correct positioning of said organism to effect therapeutic results.

21. The chair of claim 15 wherein said at least one separate accouterment device is a computer, monitor and program scroller.

22. The chair of claim 20 wherein said computer is remote from the chair and data is transferred between same via cable and radio waves.

23. The chair of claim 15 wherein adjustable synergistic combinations of vestibular stimulator, cranial electrical stimulator, exterior electrostatic resonating system, and light and sound is combined to provide means for inducing timeless/spaceless perceptions in said organism.

24. The chair of claim 21 wherein said combination has means for creating a bridge between the objective and subjective mind.

25. The chair of claim 15 wherein said accouterment device is a combined use of at least one of the following with said chair, said accouterment is combined and synchronized to create one powerful synergistically stimulating chair:
   vestibular stimulator;
   cranial electrical stimulator;
   brain wave analyzer;
   audio frequency generator;
   visual pattern generator;
   color therapy system;
   means for providing piggy-backed frequencies to said color therapy system;
   digital speech analyzer;
   communications microphone;
   memory enhancement system;
   reality video presenter;
   exterior electrostatic resonating system;
   resonating sound system;
   subliminal input driver;
   behavior modification device combination;
   software providing means for audio programming;
   software providing means for stress management programming;
   software providing means for multi-media presentations; and
   software providing means for enhancing health.

26. The chair of claim 15 wherein said chair also has means for providing at least one of the following:
   vestibular stimulation;
   light and sound stimulation;
   cranial electrical stimulation;
   stress reduction;
   biofeedback;
   memory enhancement;
   motor skill enhancement;
   speech enhancement;
   brain wave analysis;
   digital speech analysis;
   communications;
   sound resonation;
   subliminal input;
   color therapy;
   color therapy with piggy-backed frequencies;
   exteriorization;
   means for bridging the subjective and objective mind;
   accelerated learning;
   behavior modification;
   reality video capability;
   databank access; and
   means for enhancing health.

27. The chair of claim 15 wherein said at least one separate accouterment device has means for vestibular stimulation.

28. The chair of claim 15 wherein said at least one separate accouterment device has means for cranial electrical stimulation.

29. The chair of claim 15 wherein said at least one separate accouterment device has means for brain wave analysis and hard-copy printer.

30. The chair of claim 15 wherein said at least one separate accouterment device has an audio frequency generator.

31. The chair of claim 15 wherein said at least one separate accouterment device has a visual pattern generator.

32. The chair of claim 15 wherein said at least one separate accouterment device has means for digital speech analysis.

33. The chair of claim 15 wherein said at least one separate accouterment device has means for providing communications via microphone.

34. The chair of claim 15 wherein said at least one separate accouterment device has means for providing reality video capability.

35. The chair of claim 15 wherein said at least one separate accouterment device has a mix of devices calculated to provide means for inducing behavior modification.

36. The chair of claim 15 wherein said at least one separate accouterment device has software providing means for audio programming.

37. The chair of claim 15 wherein said at least one separate accouterment device has software providing means for stress management programnming.

38. The chair of claim 15 wherein said at least one separate accouterment device has software providing means for multimedia presentations for accelerated learning.

39. The chair of claim 15 wherein said at least one separate accouterment device has means for light and sound stimulation.

40. The chair of claim 15 wherein said at least one separate accouterment system has means for sound resonance enhancement.

41. The chair of claim 15 wherein said at least one separate accouterment device has means for providing color therapy.

42. The chair of claim 15 wherein said at least one separate accouterment device has means for providing color therapy with piggy-backed frequencies.

43. The chair of claim 15 wherein said at least one separate accouterment device has a subliminal input driver.

44. The chair of claim 15 wherein said at least one separate accouterment device has means for providing databank access.

45. The chair of claim 15 wherein said at least one separate accouterment device has means for providing memory enhancement.

46. The chair of claim 15 wherein said at least one separate accouterment device has means for providing exteriorization experiences.

47. The chair of claim 15 wherein said at least one separate accouterment device has means for providing biofeedback.

48. The chair of claim 15 wherein said at least one separate accouterment device has means for providing stress reduction.

49. The chair of claim 15 wherein said at least one separate accouterment device has means for bridging the objective and subjective mind.

50. The chair of claim 15 wherein said at least one separate accouterment device has means for enhancing health.

* * * * *